United States Patent [19]
Ohringer

[11] 3,955,423
[45] May 11, 1976

[54] LIQUID SAMPLING METHOD

[75] Inventor: Philip Ohringer, Melville, N.Y.

[73] Assignee: Marvin Padover, Huntington, N.Y.; a part interest

[22] Filed: Sept. 27, 1974

[21] Appl. No.: 510,094

Related U.S. Application Data

[63] Continuation-in-part of Ser. No. 290,039, Sept. 18, 1972, Pat. No. 3,846,077.

[52] U.S. Cl. .......................... 73/425.4 R; 23/230 B; 210/359; 210/DIG. 23
[51] Int. Cl.² .................. B01D 33/00; B01L 11/00
[58] Field of Search ........ 73/421, 425.4 R, 425.4 P, 73/425.6, 53, 61 R, 61.1 R, 61.4, 64.1; 23/230 B, 258.5, 259; 210/359, DIG. 23; 141/1

[56] References Cited
UNITED STATES PATENTS

| | | | |
|---|---|---|---|
| 3,481,477 | 12/1969 | Farr | 23/258.5 X |
| 3,512,940 | 5/1970 | Shapiro | 73/61 R X |
| 3,586,064 | 6/1971 | Brown et al. | 73/425.4 R X |
| 3,661,265 | 5/1972 | Greenspan | 23/258.5 X |
| 3,693,804 | 9/1972 | Grover | 210/359 |
| 3,799,342 | 3/1974 | Greenspan | 210/359 X |
| 3,832,141 | 8/1974 | Haldopoulos | 23/259 |
| 3,837,376 | 9/1974 | Brown et al. | 141/1 |

Primary Examiner—Richard C. Queisser
Assistant Examiner—Joseph W. Roskos
Attorney, Agent, or Firm—Allison C. Collard

[57] ABSTRACT

An improved method for isolating a liquid sample from a specimen container employing an elongated cylindrical tube, sized for insertion into the specimen container, and having a hollow neck formed at one end of the tube. A thin, flexible circular disc projects from the neck for slidable sealing engagement with the internal cylindrical wall of the specimen container. A shoulder is formed on the neck adjacent to the circular disc for engaging and supporting at least a portion of the disc to maintain the seal during insertion and release it during withdrawal of the tube. A removable sample measuring cup on the other end of the tube provides control of an air vent in the tube and instantaneous and easy transfer of the collected sample. The container also desirably includes a filter disposed in said neck aperture to limit the fluid flow from the tube.

11 Claims, 6 Drawing Figures

LIQUID SAMPLING METHOD

This application is a continuation-in-part of my copending application Ser. No. 290,039 filed Sept. 18, 1972 now U.S. Pat. No. 3,846,077.

The present invention relates to methods for separating a sample from a liquid specimen. The novel techniques are especially adapted for use with a particular apparatus combination described herein, and are useful in separating a portion of the upper layer of a composite liquid specimen made up of liquid layers. One important embodiment of the invention is directed at isolating the serum or plasma from the formed elements of blood after these constituents have been separated into two layers, and includes filtering the serum or plasma from a separated blood sample.

When blood specimens are tested in clinical laboratories, it is frequently necessary to obtain a cell-free sample of blood serum or plasma after the serum has been separated from the suspended cellular material. The cellular material or blood cells are separated preferably by centrifugal force driving the cells to the bottom of the tube containing the blood specimen. The serum or plasma which remains in the top portion of the tube is then removed and clinically tested. It is important to remove the serum or plasma within a short time after the blood cells are separated since these cells will begin to liberate potassium and other contaminants which may interfere with the tests to be performed.

Blood samples are generally taken in a specimen tube, such as the "Vacutainer" manufactured by Becton-Dickinson Company. After these samples are delivered to the testing laboratory, they are mechanically centrifuged to separate the blood cells from the clear liquid in the sample. The serum can then be drawn off with a conventional syringe, decanted by pouring the serum off, drawn off by pipettes, or collected by using a plunger-like apparatus which is inserted into the specimen tube. Over the past few years, a great many advances have taken place in the development of plunger-like tubes for removing the serum or plasma from the blood sample. All of the plunger-like collection devices of the prior patented art suffer from the disadvantages that they are expensive to manufacture and assemble, they are difficult to withdraw from the specimen tube due to the suction, and require additional functional parts to accomplish the separation of the clear liquid from the blood sample. Moreover, none of the aforesaid apparatus units are constructed or arranged for the instantaneous and foolproof delivery of the collected sample into a removable sample cup on the end of the collection tube by simply inverting the tube so that there is no pouring into a separate container with the attendant risks of contamination from the atmosphere and also spillage. Certain devices in current use can't be retracted with the serum.

The present invention relates to an improved method for isolating a liquid sample from a specimen container using an elongated cylindrical collection tube. When the tube is inserted into the specimen container, its plunger-like disc will contact and be supported by an abutment to form a seal against the internal wall of the specimen container. When the tube is withdrawn from the specimen container, the disc will separate from the abutment and release the seal at the container wall. The sample collected in the tube may be instantaneously transferred to a sample measuring cup installed on the opposite end of the tube after the tube is inverted.

It is therefore an object according to the present invention to provide an improved method for using a blood serum collection tube having a means for isolating the serum from a blood sample.

Still other objects and features of the present invention will become apparent from the following detailed description considered in connection with the accompanying drawings which disclose the embodiments of the invention. It is to be understood, however, that the drawings are designed for the purpose of illustration only and not as a definition of the limits of the invention.

In the drawings wherein similar reference characters denote similar elements throughout the several views.

Figure 1:
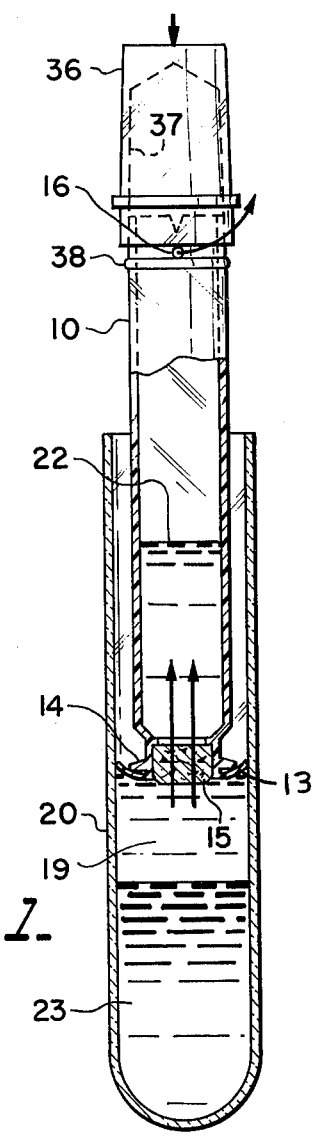
FIG. 1 is a detailed cross sectional view showing the step of filling the collection tube.
Figure 2:
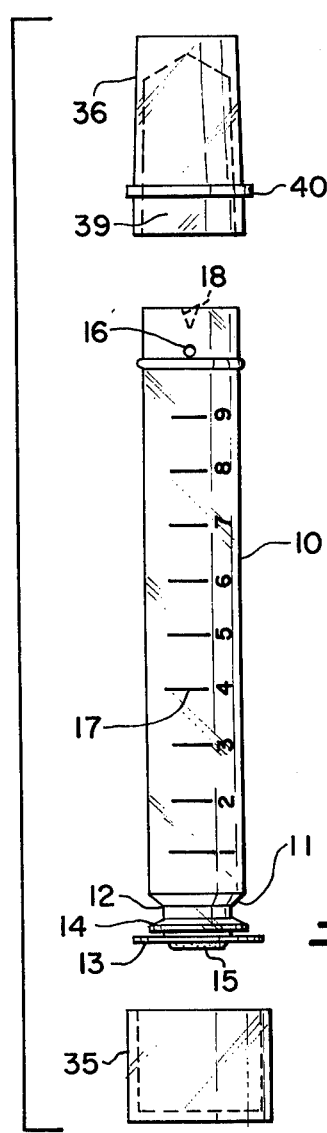
FIG. 2 is an elevation view of the collection tube with associated end caps.

Referring to FIGS. 1 and 2, there is shown a collection tube 10 having a plurality of graduations 17 formed along the walls of the tube, preferably in such units of measurement as milliliters. Optionally, the top of this tube has an air escape notch or opening 18. The bottom end of the collection tube 10 is formed with a funnel-like taper 11 terminating in a hollow plunger. The plunger has a cylindrical neck or base 12 coupled to the end of tapering section 11 and there is an externally projecting flange or shoulder 14 on the neck adjacent to and extending partially over a projecting flexible disc or wafer 13 of larger diameter than shoulder 14. In the hollow center of the plunger is disposed a filter 15 formed of a sponge-like porous material, such as a plastic foam. In a preferred embodiment, inwardly projecting shoulder 14 or ledges formed at the top and bottom of the aperture in cylindrical neck 12 secure filter 15 against accidentally becoming dislodged.

In FIG. 1, the collection tube 10 is shown inserted into a specimen tube 20, such as a "Vacutainer," that holds a separated blood sample. This sample consists of a serum or plasma layer 19 above a layer 23 of blood cells. As indicated by the upwardly directed arrows, the downward push on the collection tube overcomes the resistance of filter 15 and forces the liquid in layer 19 through the filter and into the collection tube 10 as a clear filtered liquid 22. In the downward motion of collection tube 10, plunger disc 13 is in sealing contact with the internal wall of specimen container 20. Shoulder 14 supports much of the area of disc 13 to maintain a sliding seal for the plunger to prevent any of sample 19 from passing around the edge of disc 13. The air displaced by the entering liquid can easily leave tube 10 through the vent hole 16 or the V-shaped opening 18. The side wall hole 16 is located a short distance below the top end of the tube, so that it allows air to escape during the collection of a sample even when the upper end of tube 10 is loosely covered with a sample measuring cup.

Figure 3:
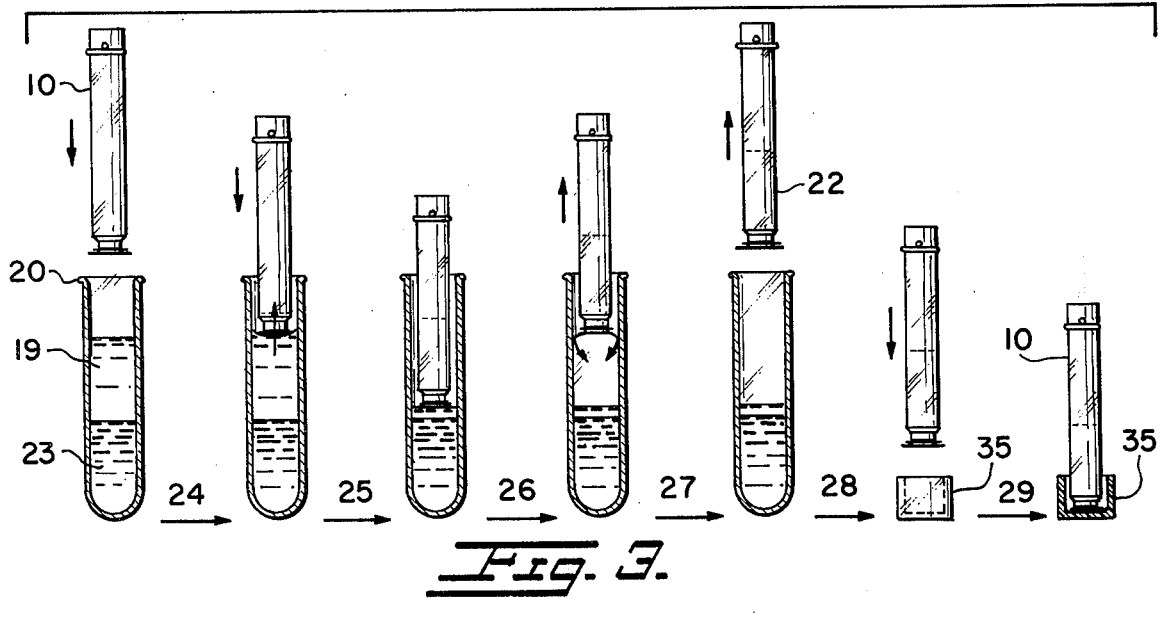
FIG. 3 shows in elevation, partly in section, the early stages of one operating procedure for removing serum or plasma from the separated blood sample contained in the specimen tube.

One embodiment of a method for isolating a plasma or serum from a blood sample is illustrated in FIG. 3. In the first diagram at the left of FIG. 3, collection tube 10 is moved downwardly toward engagement with a specimen tube 20 which contains the blood sample with its layer of separated cells 23 beneath the clear plasma layer 19. Referring to the next stage in the direction of arrow 24, as the tube 10 moves downwardly with its plunger disc 13 forming a seal against the inner wall of specimen container 20, air is initially forced through a filter 15 before the plunger disc 13 reaches the liquid 19. In the next step, filtered sample liquid 22 enters the collection tube after the exertion of a small but sufficient force to overcome the liquid resistance of the filter; and this is continued until a sample of suitable and predetermined size has been isolated in the lower end of hollow tube 10, as indicated in the stage following arrow 25. In the preferred embodiments of this invention, the quantity of the sample collected is maintained within the capacity of sample measuring cup 36 described hereinafter.

In the next stage following arrow 26, collection tube 10 is lifted upward in the direction of the vertical arrow so that circular plunger disc 13 deflects in the opposite direction away from supporting shoulder 14, thereby breaking the seal which was formed during the downward insertion motion. Inverting the plunger disc in this manner allows air to enter around the edge of disc 13 as shown by the curved arrows, and fill the increasing space on top of the remaining liquid in tube 20. There is relatively little resistance to the withdrawal of collection tube 10 from specimen container 20 because plunger disc 13 is flexibly resilient and thin; therefore little suction is created even when collection tube 10 is rapidly withdrawn. Thus, the collected serum or plasma 22 is maintained within tube 10 by the resistance of filter 15 to liquid flow. In the stages indicated by the sequence of arrows 27, 28 and 29, tube 10 with its collected liquid sample, is lifted clear of specimen tube 20 and then lowered into a sealing cap 35 of cylindrical configuration. This cap merely serves to seal and protect the aperture end of tube 10 against contamination and leakage during storage while awaiting other tests to be performed on the collected specimen or during shipping.

Figure 4:
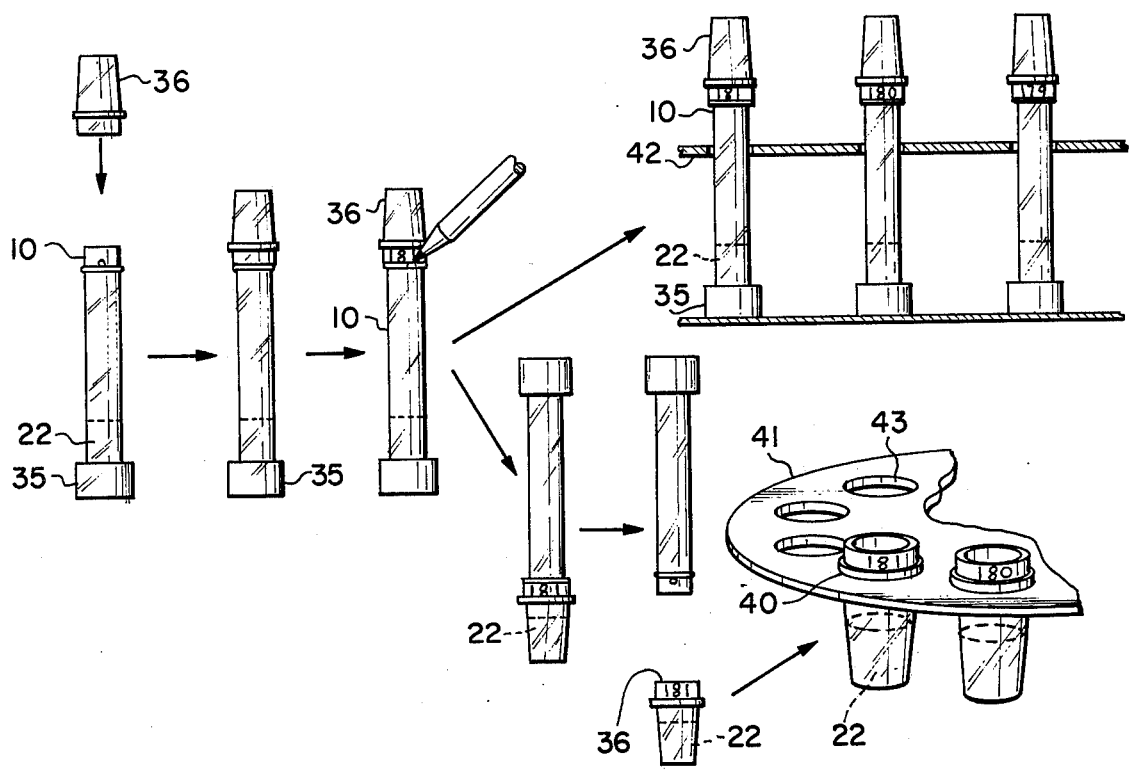
FIG. 4 is a continuation of FIG. 3 in elevation and perspective views for illustrating two alternative techniques for handling the collected samples for either storage or immediate testing.

Continuing with the procedure, in FIG. 4 a sample measuring cup 36 is placed on the open end of the tube 10 while the tube is resting in sealing cap 35. Cup 36 serves first as a protective cap against contamination by dust, etc. or reaction with the oxygen in air; and the measuring cup is marked with a number or other identifying symbol. In the lower sequential diagram of FIG. 4, the assembled tube 10 with its two caps is simply inverted to deposit liquid sample 22 into cup 36. The sample is completely protected against any contamination during its transfer to cup 36. The cup is then detached from tube 10, and deposited in tray 41 with bead 40 of the cup preventing the cup from slipping through holes 43 in this tray.

Alternately, in the upper right diagram in FIG. 4, the tube and cap assembly may be slid into a notch in the storage rack 42 for safety until there is an opportunity to invert the sample as mentioned or to pack it for shipping or mailing, e.g., to a distant clinical laboratory.

The sample measuring cup 36, as depicted in detail in FIGS. 1 and 2, is preferably a transparent or translucent resin cup which may be desirably marked with volumetric graduations similarly to tube 10. In addition to the reinforcing and supporting bead 40, this cup is also provided with a rim section 39. The inner wall 37 of the rim section is adapted to engage a raised bead 38 or other circumferential sealing surface of tube 10, and block or seal off the air vent 16 which is located on or above the sealing surface 38. Accordingly, a cup having a tapered or truncated conical configuration, on its inner surface of rim section 38, is usually preferred for a good push fit with sealing surface or rib 38.

Figure 5:
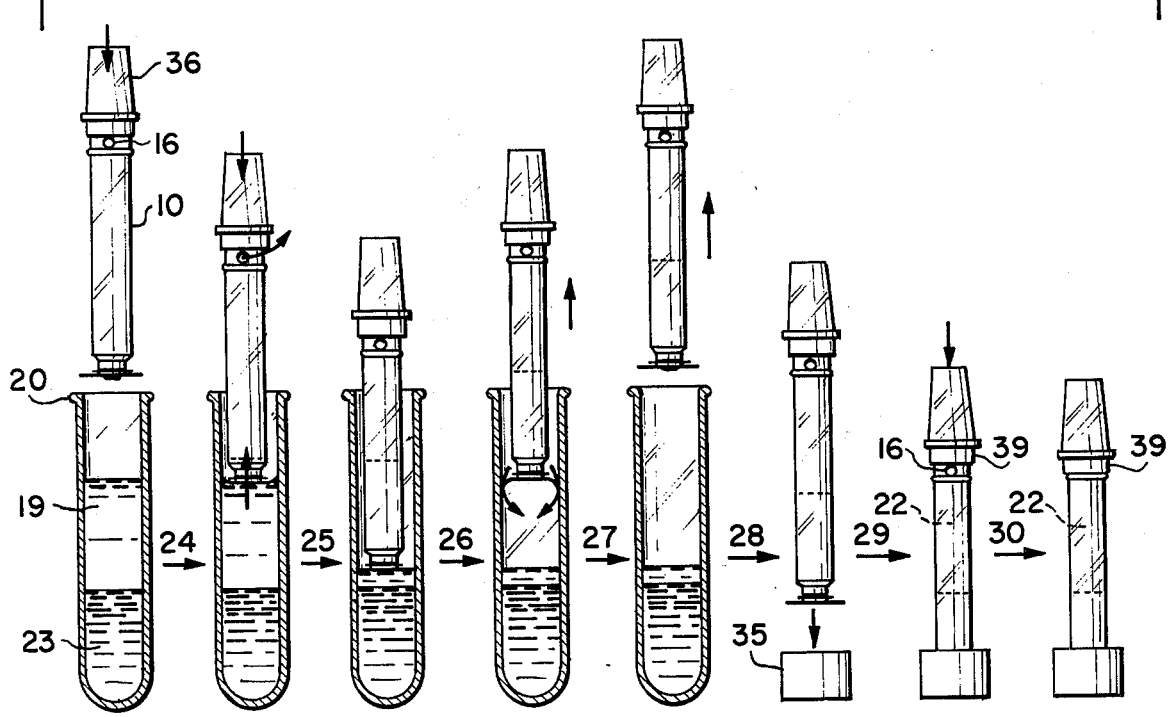
FIG. 5 shows another procedure that is similar to that of FIGS. 3 and 4 except that a measuring cup is installed on the collection tube prior to collecting the sample.
Figure 6:
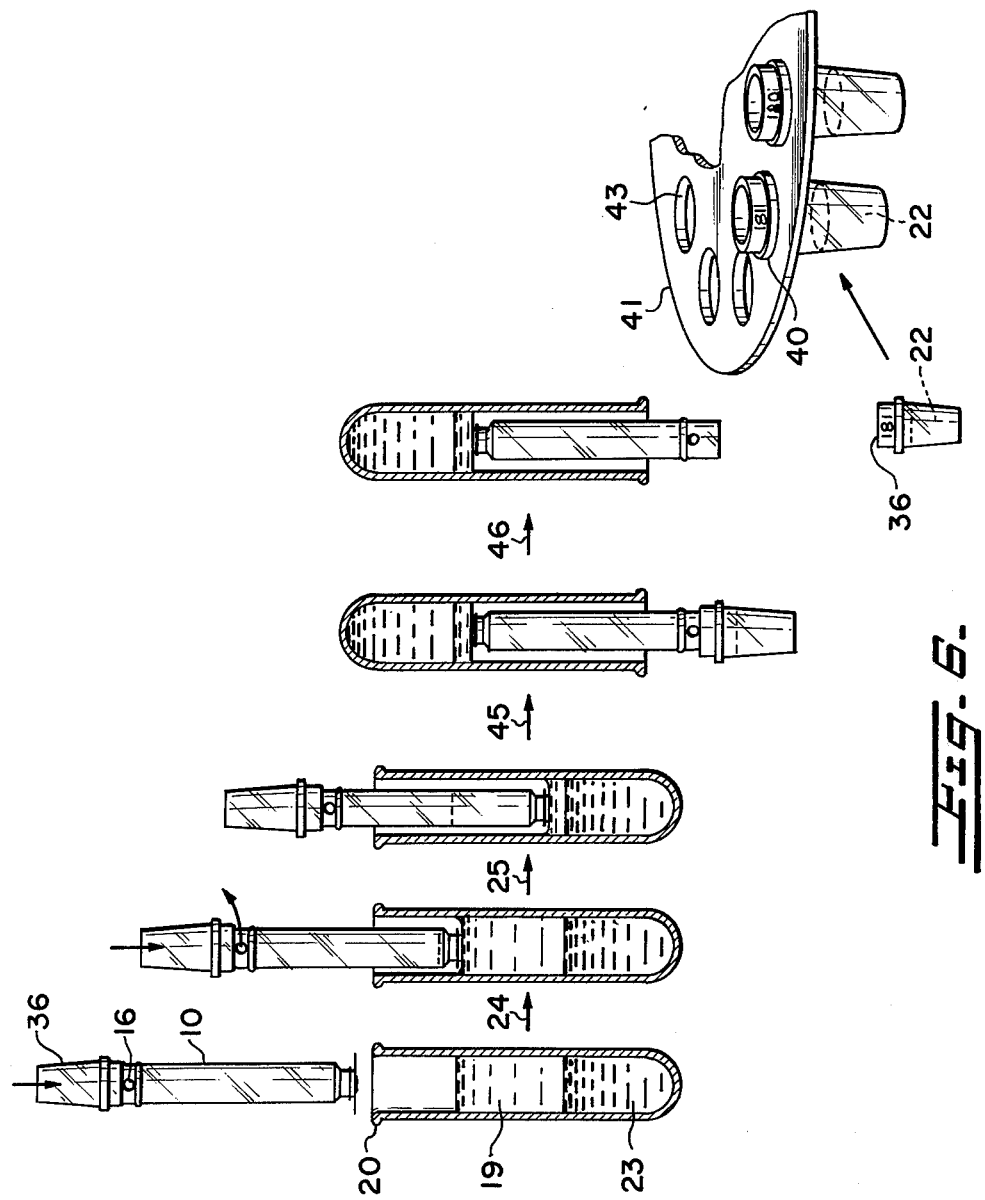
FIG. 6 shows a further embodiment of the steps of FIG. 5 wherein the tube and container are both inverted so that the sample is collected in the cup.

The process embodiment illustrated in FIG. 5 differs chiefly from the procedure of FIGS. 3 and 4 wherein the sample measuring cup is placed on tube 10 prior to inserting collection tube 10 into specimen container 20. Air vent 16 is not sealed when the cup 36 is first installed in order that air may escape while the sample liquid 22 is entering tube 10. The sequential arrows 24 to 29, inclusive, in FIG. 5 denote the same stages as in FIG. 3, and the added step following arrow 30 shows the cup 36 pushed into a lower position in which rim section 39 seals the air vent 16. Thereafter, tube 10, with its sample liquid 22 protected by cap 35, may be handled as in FIG. 4 by inverting the assembly to transfer the sample to cup 36. In still another procedural embodiment, the equipment assembly can be inverted to deposit the sample in cup 36, when the sample collecting step has been completed and without withdrawing the collection tube 10 from specimen container 20 as in stages 24, 25, 45 and 46 of FIG. 6.

Collection tube 10 is preferably of unitary construction, wherein the entire plunger assembly is molded in a single piece from resinous material before the filter is inserted into the plunger. Because the collection tube of the present invention is made from a single piece of molded plastic material so that the only additional step of manufacture involves the insertion of the filter, it is very inexpensive to manufacture and therefore, disposable after use because of its low cost. The plastic material may be any soft or resilient resin, such as polyvinylchloride, polyethylene or polypropylene; and a transparent or translucent material is generally employed to permit direct visual measuring of the sample for speed and accuracy. The diameter of the collection tube and its graduations would be preferably slightly smaller than the internal diameter of the specimen tube and plunger disc or wafer 13 would be slightly larger in diameter than the internal diameter of the specimen tube so as to form a seal when it contacts the inside walls of the specimen tube. In a preferred embodiment of the invention, the collection tube has an outside diameter of approximately 0.5 inches and the diameter of the plunger disc is approximately 0.57 inches. The edge of plunger disc 13 is approximately 0.01 inch in thickness, and it is separated from its supporting surface 14, desirably by a distance of approximately 0.01 inch. The collection tube may be approximately 4 inches in length to accommodate up to about 10 ml. of the liquid sample.

The filter is preferably constructed from a resilient cellular material, such as a plastic foam, so that it can be suitably compressed for easy insertion into the neck or base of the tube. It can also be cemented into the tube opening if mechanical retaining means are not used.

While only a few embodiments of the present invention have been shown and described, it will be obvious that many changes and modifications may be made thereunto without departing from the spirit and scope of the invention.

What is claimed is:

1. A method for isolating a liquid sample from a specimen container using a collection tube having a diameter smaller than the container and including an aperture formed at one end of the collection tube, and a flexible circular disc formed adjacent to the aperture comprising the steps of:
    inserting the collection tube into the specimen container so that the flexible disc forms a seal against the walls of the container;
    collecting a predetermined amount of liquid sample flowing through the aperture into the collection tube;
    withdrawing the tube from the container with the collected specimen;
    inverting the tube with a sample measuring cup installed on the end of said tube opposite to the collected sample to deposit the measured sample in said cup;
    installing said sample measuring cup on said tube prior to the inverting step.

2. The method according to claim 1 wherein said sample measuring cup with the measured sample therein is subsequently detached from said collection tube.

3. A method for isolating a liquid sample from a specimen container using a collection tube having a diameter smaller than the container and including an aperture formed at one end of the collection tube, and a flexible circular disc formed adjacent to the aperture comprising the steps of:
    inserting the collection tube into the specimen container so that the flexible disc forms a seal against the walls of the container;
    collecting a predetermined amount of liquid sample flowing through the aperture into the collection tube;
    withdrawing the tube from the container with the collected specimen;
    inverting the tube with a sample measuring cup installed on the end of said tube opposite to the collected sample to deposit the measured sample in said cup;
    said sample measuring cup is installed prior to the insertion step on said opposite end of said collection tube in a position wherein the wall of the cup does not seal an air vent provided in said collection tube in the vicinity and spaced from the end opposite the aperture end.

4. The method according to claim 1 wherein said collection tube is withdrawn from said specimen container after the collection of said liquid sample, and a sealing cap is installed on said apertured end of said collection tube.

5. The method according to claim 4 wherein the collection tube is inverted after the sealing cap is installed to deposit the collected sample in said sample measuring cup detachably secured to the end opposite the aperture end of the tube.

6. The method as recited in claim 1 wherein said collection tube includes a filter inserted in the aperture formed in one end.

7. The method as recited in claim 1 wherein said collection tube includes a shoulder formed adjacent to the flexible circular disc so that the shoulder supports the disc when the collection tube in inserted into the specimen container.

8. A method for isolating a liquid sample from a specimen container using a collection tube having a diameter smaller than the container and including an aperture formed at one end of the collection tube, and a flexible circular disc formed adjacent to the aperture comprising the steps of;
    inserting the collection tube into the specimen container so that the flexible disc forms a seal against the walls of the container, said tube including a sample measuring cup disposed on the end opposite to the collected sample;
    collecting a predetermined amount of liquid sample flowing through the aperture into the collection tube;
    withdrawing the tube from the container with the collected specimen;
    installing a sealing cap on the apertured end of the tube; and
    pushing the sample measuring cup further onto said collection tube to seal an air vent in the tube.

9. A method for isolating a liquid sample from a specimen container using a collection tube having a diameter smaller than the container and including an aperture formed at one end, a flexible circular disc formed adjacent to the aperture and a shoulder formed adjacent to the disc comprising the steps of:
    inserting the collection tube into the specimen container so that the flexible disc forms a seal against the walls of the container;
    measuring the collection of a predetermined amount of liquid sample flowing through the aperture into the collection tube;
    inverting the container and the tube with a sample measuring cup installed on the end of the tube opposite the aperture end so that the collected sample will be deposited in said cup;
    installing said sample measuring cup on said tube prior to the inverting step.

10. The method as recited in claim 9 wherein said collection tube includes a filter inserted in the aperture formed in one end.

11. The method as recited in claim 9 wherein said collection tube includes a shoulder formed adjacent to the flexible circular disc so that the shoulder supports the disc when the collection tube is inserted into the specimen container.

* * * * *